United States Patent
Park et al.

(10) Patent No.: US 10,253,339 B2
(45) Date of Patent: Apr. 9, 2019

(54) GLUCONATE REPRESSOR VARIANT, MICROORGANISM CONTAINING THE SAME PRODUCING L-LYSINE, AND METHOD FOR PRODUCING L-LYSINE

(71) Applicant: CJ CHEILJEDANG CORPORATION, Seoul (KR)

(72) Inventors: Sang Hee Park, Seoul (KR); Hyung Joon Kim, Seoul (KR); Nam Hyun Kim, Yangsan-si (KR); Jun Ok Moon, Seoul (KR); Jeong Seok Oh, Seoul (KR); Song-Gi Ryu, Suwon-si (KR); Hyang Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/568,385

(22) PCT Filed: Mar. 11, 2016

(86) PCT No.: PCT/KR2016/002480
§ 371 (c)(1),
(2) Date: Oct. 20, 2017

(87) PCT Pub. No.: WO2016/171392
PCT Pub. Date: Oct. 27, 2016

(65) Prior Publication Data
US 2018/0100173 A1    Apr. 12, 2018

(30) Foreign Application Priority Data
Apr. 20, 2015 (KR) .................. 10-2015-0055495

(51) Int. Cl.
| | |
|---|---|
| C12P 21/00 | (2006.01) |
| C12N 15/09 | (2006.01) |
| C12P 13/08 | (2006.01) |
| C07K 14/195 | (2006.01) |
| C07K 14/34 | (2006.01) |
| C07C 229/26 | (2006.01) |
| C12N 15/77 | (2006.01) |

(52) U.S. Cl.
CPC ............ *C12P 13/08* (2013.01); *C07C 229/26* (2013.01); *C07K 14/195* (2013.01); *C07K 14/34* (2013.01); *C12N 15/77* (2013.01)

(58) Field of Classification Search
CPC .......... A61K 38/03; C12N 15/09; C12P 21/00
See application file for complete search history.

(56) References Cited

U.S. PATENT DOCUMENTS

2013/0102037 A1*  4/2013  Lim .................. C12N 15/77
                                                435/115

FOREIGN PATENT DOCUMENTS

| CN | 1596267 A | 3/2005 |
|---|---|---|
| EP | 1 108 790 A2 | 6/2001 |
| JP | 2005-536194 A | 12/2005 |
| JP | 2012-530515 A | 12/2012 |
| KR | 10-0073610 | 5/1994 |
| KR | 10-0159812 | 8/1998 |
| KR | 2005-0026388 A | 3/2005 |
| KR | 10-0924065 B1 | 10/2009 |
| KR | 2012-0007965 A | 1/2012 |

OTHER PUBLICATIONS

Binder et al., "A high-throughput approach to identify genomic variants of bacterial metabolite producers at the single-cell level," *Genome Biology* 13:R40 (12 pages) (2012).
Frunzke et al., "Co-ordinated regulation of gluconate catabolism and glucose uptake in *Corynebacterium glutamicum* by two functionally equivalent transcriptional regulators, GntR1 and GntR2," *Molecular Microbiology* 67(2):305-322 (2008).
GenBank Accession No. CAF21189.1 (Feb. 27, 2015).
Tanaka et al., "Genome-Wide Analysis of the Role of Global Transcriptional Regulator GntR1 in *Corynebacterium glutamicum*," *Journal of Bacteriology* 196(18):3249-3258 (Sep. 2014).
Frunzke et al., "Co-ordinated regulation of gluconate catabolism and glucose uptake in *Corynebacterium glutamicum* by two functionally equivalent transcriptional regulator, GntR1 and GntR2," *Molecular Microbiology* 67(2):305-322, 2008.

* cited by examiner

*Primary Examiner* — Maryam Monshipouri
(74) *Attorney, Agent, or Firm* — Seed IP Law Group LLP

(57) ABSTRACT

The present invention relates to a novel gluconate repressor variant, a microorganism containing the same, and a method for producing L-lysine using the same.

8 Claims, No Drawings
Specification includes a Sequence Listing.

SEQUENCE LISTING

```
<160> NUMBER OF SEQ ID NOS: 8

<210> SEQ ID NO 1
<211> LENGTH: 250
<212> TYPE: PRT
<213> ORGANISM: Artificial Sequence
<220> FEATURE:
<223> OTHER INFORMATION: Variant of the gluconate repressor protein
      GntR1 (R102C)

<400> SEQUENCE: 1

Met Thr Pro Ala Asn Glu Ser Pro Met Thr Asn Pro Leu Gly Ser Ala
 1               5                  10                  15

Pro Thr Pro Ala Lys Pro Leu Leu Asp Ser Val Leu Asp Glu Leu Gly
            20                  25                  30

Gln Asp Ile Ile Ser Gly Lys Val Ala Val Gly Asp Thr Phe Lys Leu
        35                  40                  45

Met Asp Ile Gly Glu Arg Phe Gly Ile Ser Arg Thr Val Ala Arg Glu
 50                  55                  60

Ala Met Arg Ala Leu Glu Gln Leu Gly Leu Val Ala Ser Ser Arg Arg
 65                  70                  75                  80

Ile Gly Ile Thr Val Leu Pro Gln Glu Glu Trp Ala Val Phe Asp Lys
                 85                  90                  95

Ser Ile Ile Arg Trp Cys Leu Asn Asp Glu Gly Gln Arg Glu Gly Gln
            100                 105                 110

Leu Gln Ser Leu Thr Glu Leu Arg Ile Ala Ile Glu Pro Ile Ala Ala
        115                 120                 125

Arg Ser Val Ala Leu His Ala Ser Thr Ala Glu Leu Glu Lys Ile Arg
130                 135                 140

Ala Leu Ala Thr Glu Met Arg Gln Leu Gly Glu Ser Gly Gln Gly Ala
145                 150                 155                 160

Ser Gln Arg Phe Leu Glu Ala Asp Val Thr Phe His Glu Leu Ile Leu
                165                 170                 175

Arg Tyr Cys His Asn Glu Met Phe Ala Ala Leu Ile Pro Ser Ile Ser
            180                 185                 190

Ala Val Leu Val Gly Arg Thr Glu Leu Gly Leu Gln Pro Asp Leu Pro
        195                 200                 205

Ala His Glu Ala Leu Asp Asn His Asp Lys Leu Ala Asp Ala Leu Leu
    210                 215                 220

Asn Arg Asp Ala Asp Ala Ala Glu Thr Ala Ser Arg Asn Ile Leu Asn
225                 230                 235                 240

Glu Val Arg Ser Ala Leu Gly Thr Leu Asn
                245                 250

<210> SEQ ID NO 2
<211> LENGTH: 753
<212> TYPE: DNA
<213> ORGANISM: Artificial Sequence
<220> FEATURE:
<223> OTHER INFORMATION: Variant of the gluconate repressor protein
      nucleotide sequence gntR1(R102C)

<400> SEQUENCE: 2
```

```
atgaccccag caaacgaaag tcctatgact aatccattag gttctgcccc caccccagcc    60
aagccacttc ttgacagtgt tcttgatgag ctcggtcaag atatcatcag tggcaaggtt   120
gctgtcggag ataccttcaa gctgatggac atcggcgagc gttttggcat ttcccgcaca   180
gtggcacgcg aagcgatgcg cgctttggag cagctcggtc ttgtcgcttc ttcacgtcgc   240
attggcatta ctgttttgcc acaggaagag tgggctgttt ttgataagtc catcattcgc   300
tggtgtctca atgacgaagg tcagcgtgaa ggccagcttc agtctcttac cgagcttcgt   360
attgctattg aaccgattgc cgcgcgcagc gttgctcttc acgcgtcaac cgccgagctc   420
gagaaaatcc gcgcgctcgc aacagagatg cgtcagttgg gtgaatctgg tcagggtgcg   480
tcccagcgct cctcgaagc ggacgtcact ttccacgagc tcatcttgcg ttattgccac   540
aatgagatgt tcgctgcact gattccgtcg attagcgcgg ttcttgtcgg ccgcaccgag   600
ctcggcctgc agcctgatct gccggcgcac gaggcgctag acaaccacga taagcttgcc   660
gacgccctcc ttaaccgcga cgccgacgcc gcagaaactg cgtcccgaaa catcctcaat   720
gaggtgcgca gcgcgctggg cacgctgaac taa                                753
```

<210> SEQ ID NO 3
<211> LENGTH: 753
<212> TYPE: DNA
<213> ORGANISM: Corynebacterium glutamicum

<400> SEQUENCE: 3

```
atgaccccag caaacgaaag tcctatgact aatccattag gttctgcccc caccccagcc    60
aagccacttc ttgacagtgt tcttgatgag ctcggtcaag atatcatcag tggcaaggtt   120
gctgtcggag ataccttcaa gctgatggac atcggcgagc gttttggcat ttcccgcaca   180
gtggcacgcg aagcgatgcg cgctttggag cagctcggtc ttgtcgcttc ttcacgtcgc   240
attggcatta ctgttttgcc acaggaagag tgggctgttt ttgataagtc catcattcgc   300
tggcgtctca atgacgaagg tcagcgtgaa ggccagcttc agtctcttac cgagcttcgt   360
attgctattg aaccgattgc cgcgcgcagc gttgctcttc acgcgtcaac cgccgagctc   420
gagaaaatcc gcgcgctcgc aacagagatg cgtcagttgg gtgaatctgg tcagggtgcg   480
tcccagcgct cctcgaagc ggacgtcact ttccacgagc tcatcttgcg ttattgccac   540
aatgagatgt tcgctgcact gattccgtcg attagcgcgg ttcttgtcgg ccgcaccgag   600
ctcggcctgc agcctgatct gccggcgcac gaggcgctag acaaccacga taagcttgcc   660
gacgccctcc ttaaccgcga cgccgacgcc gcagaaactg cgtcccgaaa catcctcaat   720
gaggtgcgca gcgcgctggg cacgctgaac taa                                753
```

<210> SEQ ID NO 4
<211> LENGTH: 250
<212> TYPE: PRT
<213> ORGANISM: Corynebacterium glutamicum

<400> SEQUENCE: 4

```
Met Thr Pro Ala Asn Glu Ser Pro Met Thr Asn Pro Leu Gly Ser Ala
 1               5                  10                  15

Pro Thr Pro Ala Lys Pro Leu Leu Asp Ser Val Leu Asp Glu Leu Gly
            20                  25                  30

Gln Asp Ile Ile Ser Gly Lys Val Ala Val Gly Asp Thr Phe Lys Leu
        35                  40                  45

Met Asp Ile Gly Glu Arg Phe Gly Ile Ser Arg Thr Val Ala Arg Glu
```

```
              50                  55                  60
Ala Met Arg Ala Leu Glu Gln Leu Gly Leu Val Ala Ser Ser Arg Arg
 65                  70                  75                  80

Ile Gly Ile Thr Val Leu Pro Gln Glu Glu Trp Ala Val Phe Asp Lys
                 85                  90                  95

Ser Ile Ile Arg Trp Arg Leu Asn Asp Glu Gly Gln Arg Glu Gly Gln
            100                 105                 110

Leu Gln Ser Leu Thr Glu Leu Arg Ile Ala Ile Glu Pro Ile Ala Ala
        115                 120                 125

Arg Ser Val Ala Leu His Ala Ser Thr Ala Glu Leu Glu Lys Ile Arg
    130                 135                 140

Ala Leu Ala Thr Glu Met Arg Gln Leu Gly Glu Ser Gly Gln Gly Ala
145                 150                 155                 160

Ser Gln Arg Phe Leu Glu Ala Asp Val Thr Phe His Glu Leu Ile Leu
                165                 170                 175

Arg Tyr Cys His Asn Glu Met Phe Ala Ala Leu Ile Pro Ser Ile Ser
            180                 185                 190

Ala Val Leu Val Gly Arg Thr Glu Leu Gly Leu Gln Pro Asp Leu Pro
        195                 200                 205

Ala His Glu Ala Leu Asp Asn His Asp Lys Leu Ala Asp Ala Leu Leu
    210                 215                 220

Asn Arg Asp Ala Asp Ala Ala Glu Thr Ala Ser Arg Asn Ile Leu Asn
225                 230                 235                 240

Glu Val Arg Ser Ala Leu Gly Thr Leu Asn
                245                 250

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tcagggtgta gcggttcggt ttat                                          24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ccgcgcgtaa tacgactcac tata                                          24

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
aagaattcag cagatcgaag aagaagc                                       27

<210> SEQ ID NO 8
<211> LENGTH: 25
<212> TYPE: DNA
<213> ORGANISM: Artificial Sequence
```

```
<220> FEATURE:
<223> OTHER INFORMATION: Primer

<400> SEQUENCE: 8
aagtcgacgg gactaaaagc tggcg                                          25
```

GLUCONATE REPRESSOR VARIANT, MICROORGANISM CONTAINING THE SAME PRODUCING L-LYSINE, AND METHOD FOR PRODUCING L-LYSINE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_433USPC_SEQUENCE_LISTING.txt. The text file is 7.3 KB, was created on Oct. 18, 2017, and is being submitted electronically via EFS-Web.

TECHNICAL FIELD

The present invention relates to a novel gluconate repressor variant, a microorganism containing the same, and a method for producing L-lysine using the same.

BACKGROUND ART

For the mass production of useful products such as amino acids, regulation of glucose uptake and pentose phosphorylation pathway in the *Corynebacterium* strain is very important (Handbook of *Corynebacterium glutamicum*. 2005. 215-240).

Gluconate repressor (GntR) is an important regulatory protein that regulates carbon flow through glucose uptake and pentose phosphorylation pathways. It is known that two gluconate repressors (GntR1 and GntR2) are found in the *Corynebacterium glutamicum* strain.

GntR1 and GntR2 strongly inhibit the expression of genes encoding gluconate permease (gntP), gluconate kinase (gntK), and 6-phosphogluconate dehydrogenase (gnd) which are related to gluconate metabolism, and serve a role of weakly inhibiting the expression of tkt-tal-zwf-opcA-devB operon, which is a major gene of the pentose phosphorylation pathway. Meanwhile, the expression of genes encoding glucose-specific transporter enzyme II (ptsG) and sucrose-specific transporter enzyme II (ptsS) of phosphotransferase system (PTS), which is a major sugar-infusion metabolic pathway of the *Corynebacterium* strain, is promoted to be significantly involved in sugar infusion (Julia Frunzke, Verena Engels, Sonja Hasenbein, Cornelia Gatgens and Michael Bott, *Molecular Microbiology* (2008) 67(2), 305-322).

DISCLOSURE

Technical Problem

The present inventors have tried to find a gene that has an effective effect on L-lysine productivity and developed a novel variant gluconate repressor 1 (GntR1), and it was confirmed that the microorganism containing the same producing L-lysine, compared to the microorganism comprising wild-type gluconate repressor 1, enhanced sugar consumption rate and L-lysine productivity, and thereby the present inventors completed the invention.

Technical Solution

An object of the present invention is to provide a novel variant of the gluconate repressor protein.

Another object of the present invention is to provide a polynucleotide encoding the variant and an expression vector comprising the polynucleotide.

Still another object of the present invention is to provide a microorganism producing L-lysine, which expresses a variant of the gluconate repressor protein.

Yet another object of the present invention is to provide a method for producing L-lysine comprising: (a) culturing the microorganism producing L-lysine in a medium; and (b) recovering L-lysine from the cultured microorganism or the medium in step (a).

Advantageous Effects

The microorganism containing a gluconate repressor variant producing L-lysine according to the present invention exhibits an improved sugar consumption rate as compared with the microorganism not containing the variant and can lead to effective production of L-lysine. In particular, L-lysine is an essential amino acid of animal feed and is required to be industrially mass produced, and when L-lysine is produced with high efficiency according to the present invention, it can also reduce the cost of producing feed.

BEST MODE

An embodiment of the present invention provides a novel variant of the gluconate repressor protein.

As used herein, the term "gluconate repressor protein" refers to a regulatory protein involved in gluconate metabolism or sugar uptake. The gluconate repressor protein is not particularly limited, but may be a microorganism belonging to the genus *Corynebacterium*, specifically, a gluconate repressor protein derived from *Corynebacterium glutamicum*. More specifically, the gluconate repressor protein may be GntR1 protein derived from *Corynebacterium glutamicum*, but is not limited thereto. The gluconate repressor protein may be, but is not limited to, GntR1 comprising the amino acid sequence of SEQ ID NO: 4. For example, the gluconate repressor protein may be an amino acid sequence comprising an amino acid sequence of SEQ ID NO: 4 and having a homology of at least 80%, specifically at least 90%, more specifically at least 95%, and even more specifically at least 99%. In addition, the gluconate repressor protein comprising the amino acid sequence of SEQ ID NO: 4 may be encoded by the gntR1 gene comprising the nucleotide sequence of SEQ ID NO: 3, but is not limited thereto. For example, it may be the nucleotide sequence of SEQ ID NO: 3 or may be a nucleotide sequence having a homology of at least 80%, specifically at least 90%, more specifically at least 95%, or even more specifically at least 99%.

As used herein, the term "homology" refers to the percentage of identity between two polynucleotides or polypeptide moieties. The homology between sequences from one moiety to another moiety can be determined by known techniques. For example, homology can be determined by aligning sequence information and directly aligning the sequence information between two polynucleotide molecules or two polypeptide molecules using a computer program that is already available. The computer program may be BLAST (NCBI), CLC Main Workbench (CLC bio), MegAlign™ (DNASTAR Inc.), etc. Further, homology between polynucleotides can be determined by hybridizing polynucleotides under conditions that form a stable double strand between homologous regions, then resolving the single-strand-specific nucleases to determine the size of the resolved fragment.

The variant of the gluconate repressor protein may be a polypeptide in which arginine (R), which is the $102^{nd}$ amino acid in the amino acid sequence of SEQ ID NO: 4, is substituted with an amino acid other than arginine. Specifically, the variant of the gluconate repressor protein may be a polypeptide comprising an amino acid sequence of SEQ ID NO: 1, wherein the amino acid at position 102 is substituted with cysteine (C).

Such a variant of the gluconate repressor protein includes not only a polypeptide comprising an amino acid sequence of SEQ ID NO: 1, but also a variant having a homology of 80% or more, specifically 90% or more, more specifically 95% or more, even more specifically 99% or more, and substantially, it is obvious that an amino acid sequence having biological activity identical to or corresponding to a protein having an amino acid sequence of SEQ ID NO: 1, even in cases where some of the sequences have deletion, modification, substitution, or addition of amino acid sequences, is included in the scope of the present invention.

Another embodiment of the present invention is a polynucleotide encoding a variant of the gluconate repressor protein and an expression vector comprising the polynucleotide.

The gluconate repressor protein and a variant thereof are as described above.

Specifically, a polynucleotide encoding a variant of the gluconate repressor protein may be a polynucleotide encoding a protein comprising an amino acid sequence of SEQ ID NO: 1, or may be a polynucleotide having a homology of at least 80%, specifically at least 90%, more specifically 95%, even more specifically at least 99%. The polynucleotide encoding a variant of the gluconate repressor protein may have, for example, the nucleotide sequence of SEQ ID NO: 2, but is not limited thereto.

As used herein, the term "polynucleotide" refers to a polymer of nucleotides in which the nucleotide unit is linked in a long chain by covalent bonds. Generally, it refers to DNA or RNA strands longer than a certain length. The polynucleotide may have a variety of nucleotide sequences that encode the same amino acid sequence due to genetic code degeneracy of the genetic code. In addition, codon-optimized sequences may be employed to optimize expression depending on the type of host cells.

As used herein, the term "vector" refers to any nucleic acid molecule for cloning and/or transfer of a polynucleotide to a host cell. A vector may be a replicon that can bring about the replication of a joined fragment of another DNA fragment. A "replication unit" refers to any genetic unit (e.g., plasmid, phage, cosmid, chromosome, and virus). In the present invention, the vector is not particularly limited as long as it is replicable in a host, and any vector known in the art can be used. The vector used to construct the recombinant vector may be a plasmid, a cosmid, a virus, and a bacteriophage in a natural or recombinant state. For example, pWE15, M13, λEMBL3, λEMBL4, λFIXII, λDASHII, λZAPII, λgt10, λgt11, Charon4A, Charon21A, etc. can be used as the phage vector or cosmid vector, and as the plasmid vector, pDZ vector, pBR system, pUC system, pBluescriptII system, pGEM system, pTZ system, pCL system, pET system, etc. can be used. The available vectors are not particularly limited, and known expression vectors can be used. Specifically, pDZ (Korean Registered Patent No. 10-0924065; incorporated herein by reference in its entirety) may be used, but is not limited thereto.

As used herein, the term "transformation" is carried out by introducing a polynucleotide encoding a variant of the gluconate repressor protein into a host cell so that the polynucleotide can be expressed in the host cell, and the polynucleotide which is transformed, as long as it can be expressed in the host cell, includes, without limitation, those which are inserted in a chromosome or located outside the chromosome.

The polynucleotide may be introduced into the host cell in the form of an expression cassette, which is a construct containing all elements necessary for expression by itself. The expression cassette can generally include a promoter operably linked to the gene, a transcription termination signal, a ribosome binding site, and a translation termination signal. The expression cassette may be in the form of an expression vector capable of self-replication. Further, the polynucleotide may be introduced into the host cell itself or in the form of an expression cassette and operatively linked to the sequence necessary for expression in the host cell, but is not limited thereto.

Another embodiment of the present invention is a microorganism producing L-lysine which expresses a variant of the gluconate repressor protein.

The gluconate repressor protein and a variant thereof have been described above.

As used herein, the term "L-lysine" is an essential amino acid that is not synthesized in the body as a basic α-amino acid and refers to a kind of L-amino acid having the chemical formula $NH_2(CH_2)_4CH(NH_2)COOH$. L-Lysine is biosynthesized from oxaloacetic acid through the lysine biosynthetic pathway, and NADPH-dependent reductase catalyzes the intermediate process for lysine biosynthesis. In the course of L-lysine biosynthesis of one molecule, three molecules of NADPH are directly consumed by the sugar enzymes, and one molecule of NADPH is indirectly used.

The microorganism may include variants of the gluconate repressor protein by mutation or may be transformed with a vector comprising a polynucleotide encoding a variant of the gluconate repressor protein.

The microorganism includes a protein having mutant activity of the gluconate repressor protein or a prokaryotic microorganism and eukaryotic microorganism if the microorganism is transformed so that the glycosyltransferase protein is expressed. For example, microorganism strains such as the genus *Escherichia*, the genus *Erwinia*, the genus *Serratia*, the genus *Providencia*, the genus *Enterobacteria*, the genus *Salmonella*, the genus *Streptomyces*, the genus *Pseudomonas*, the genus *Brevibacterium*, or the genus *Corynebacterium*, etc. may be included. Specifically, they may be microorganisms belonging to the genus *Corynebacterium*, and more specifically, *Corynebacterium glutamicum*, but are not limited thereto.

When the mutant protein of the gluconate repressor protein of the present invention is contained in the microorganism producing L-lysine, L-lysine production capacity can be increased by effectively consuming the saccharide as compared with the microorganism containing the wild-type gluconate repressor protein.

The microorganism producing L-lysine may include any type of microorganism if it has L-lysine producing ability, and includes all forms of natural strains and recombinant strains.

The microorganism of the genus *Corynebacterium* capable of having L-lysine producing ability may be a mutant strain resistant to the L-lysine analogue. L-Lysine analogues inhibit the growth of Coryne microorganisms, but such inhibition is completely or partially cleared when L-lysine coexists in the medium. Examples of the L-lysine analogues include oxa L-lysine, L-lysine hydroxamate, S-(2-aminoethyl)-L-cysteine (AEC), γ-methyl L-lysine, α-chlorocaprolactam, etc., but are not limited thereto. The variant having resistance to such L-lysine analogues can be obtained by treating the microorganism of the genus *Corynebacterium* with a conventional artificial mutagenesis treatment, but is not limited thereto. Non-limiting examples of this include *Corynebacterium glutamicum* KCCM11016P (Korean Registered Patent No. 10-0159812), *Corynebacterium glutamicum* KFCC 11001, and *Corynebacterium glutamicum* KCCM11347P (Korean Registered Patent No. 10-0073610), but are not limited thereto.

In addition, the microorganism of the genus *Corynebacterium* having L-lysine producing ability may be modified such that the activity of the L-lysine biosynthesis-related protein is enhanced as compared with non-modified strains. That is, the expression of one or more types of L-lysine biosynthesis-related genes is enhanced. Such expression enhancement may include, but is not limited to, gene amplification, replacement or alteration of sequences such as promoters or initiation codons, introduction of modifications to improve expression, etc. Non-limiting examples of this include *Corynebacterium glutamicum* CJ3P (Binder et al. *Genome Biology* 2012, 13:R40), but are not limited thereto.

In addition, examples of the L-lysine biosynthesis-related gene include genes located on the L-lysine biosynthetic pathway, and specifically, dihydrodipicolinic acid synthase gene (dapA), aspartokinase gene (lysC), dihydrodipicolinic acid reductase gene (dapB), diaminopimelate decarboxylase gene (lysA), diaminopimelate dehydrogenase gene (ddh), phosphoenolpyruvate carboxylase gene (ppc), aspartate semialdehyde dehydrogenase gene (asd), aspartase gene (aspA), and pyruvate carboxylase (pyc), but are not limited thereto. Further, transketolase (tkt) present on the pentose phosphate pathway, etc. may be referenced, but the gene is not limited thereto.

Meanwhile, the microorganism of the genus *Corynebacterium* which can have the L-lysine producing ability by including modifications known in the art associated with L-lysine production, but is not limited thereto.

Another aspect of the present invention is a method for producing L-lysine comprising: (a) culturing a microorganism producing L-lysine in a medium; and (b) recovering L-lysine from the cultured microorganism or culture medium in step (a).

The L-lysine and the microorganism producing it are as described above.

As used herein, the term "culture" refers to cultivation of the microorganism under moderately artificially controlled environmental conditions. The culturing process of the present invention can be carried out according to a suitable culture medium and culture conditions known in the art. Conditions such as the specific culture temperature, incubation time, and pH of the medium can be carried out according to the general knowledge of the person skilled in the art or according to conventionally known methods. Specifically, these known culture methods are described in [Chmiel; Bioprozesstechnik 1. Einfuhrung indie Bioverfahrenstechnik (Gustav Fischer Verlag, Stuttgart, 1991), and Storhas; Bioreaktoren and periphere Einrichtungen (Vieweg Verlag, Braunschweig/Wiesbaden, 1994)]. Further, the culture method includes a batch culture, a continuous culture, and a fed-batch culture. Specifically, a batch process or a fed batch or a repeated fed batch process can be continuously cultured, but the culturing process is not limited thereto.

The medium used for culture shall meet the requirements of specific strains in a proper manner. Carbon sources which may be used for the medium include saccharides and carbohydrates such as glucose, saccharose, lactose, fructose, maltose, starch, cellulose, etc.; oil and fat such as soybean oil, sunflower oil, castor oil, coconut oil, etc.; fatty acid such as palmitic acid, stearic acid, linoleic acid, etc.; glycerol; alcohol such as ethanol; and organic acid such as acetic acid, but are not limited thereto. These substances can be used individually or as a mixture and are not limited thereto. Nitrogen sources which may be used include peptone, yeast extract, gravy, malt extract, corn steep liquor, soybean meal, and urea or inorganic compounds, for example, ammonium sulfate, ammonium chloride, ammonium phosphate, ammonium carbonate, ammonium nitrate, etc., but are not limited thereto, and nitrogen sources can also be used individually or as a mixture. Available phosphate sources include potassium dihydrogen phosphate, dipotassium hydrogen phosphate, or corresponding sodium-containing salts, etc. but are not limited thereto. Further, the culture medium may contain metallic salts such as magnesium sulfate or iron sulfate, but the salts are not limited thereto. Finally, in addition to the above materials, essential growth substances such as amino acids and vitamins may be used. Further, appropriate precursors may be used for the culture medium. Raw materials described above may be added batch-wise or continuously to an incubator in the incubation process, but are not limited thereto.

In addition, chemical compounds such as ammonium hydroxide, potassium hydroxide, ammonia, phosphoric acid, and sulfuric acid may be appropriately added to the incubator during culture to adjust the pH of the culture medium. During incubation, production of bubbles can be inhibited by using antifoaming agents such as fatty acid polyglycol. Further, in order to maintain the aerobic condition of the incubator or incubation, oxygen or oxygen-containing gas can be added to the incubator, or in order to maintain anaerobic conditions, nitrogen, hydrogen, or carbon dioxide gas may be injected or gas may not be injected. The temperature of the incubation is typically between 20° C. to 40° C., specifically 30° C. to 35° C., but is not limited thereto. The incubation period can be continued until the desired amount of useful material is achieved, and specifically may be 10 hours to 100 hours. L-Lysine may be excreted from the culture medium or included in microorganisms.

In addition, methods for producing L-lysine of the present invention or methods for recovering L-lysine from the culture medium are widely known in the art. For the methods for recovering L-lysine, filtration, negative ion exchange chromatography, crystallization, and HPLC, etc. may be used, but the methods are not limited to these examples.

BEST MODE

Hereinbelow, the present invention will be described in more detail through the following Examples. However, these Examples are intended to illustrate the present invention in an exemplary manner, and the scope of the present invention is not limited to these Examples.

Example 1: Preparation of Recombinant *Corynebacterium glutamicum* Genomic DNA Library In the present Example, in order to discover the producing ability of L-lysine and genes and variations that discover beneficial effects to productivity, after inducing artificial mutations on *Corynebacterium glutamicum* ATCC13032 strains by N-methyl-N-nitro-N-nitroguanidine (NTG), genomic DNA was extracted by extraction methods conventionally known in the art. Restriction enzyme Sau3AI was applied to the prepared DNA obtain partial fragments having a size of 1 kb to 3 kb. After connecting the fragments to transformant shuttle vector pECCG122 to *E. coli* and *Corynebacterium* to restriction enzyme BamHI end, they were transformed to *E. coli* DH5a and smeared to LB solid medium including kanamycin (25 mg/L). After selecting colonies transformed into vectors inserted with the fragments through PCR (using primers of SEQ ID NOs: 5 and 6), all of these were mixed together to extract plasmids by a commonly known extraction method.

```
SEQ ID NO:
TCAGGGTGTAGCGGTTCGGTTTAT

SEQ ID NO:
CCGCGCGTAATACGACTCACTATA
```

Example 2: Introduction of Artificial Variant Library and L-Lysine Producing Ability Enhancement By having KCCM11016P strain as a parent strain (the microorganism was disclosed as KFCC10881 and re-deposited into an international depository institution under the Budapest Treaty and assigned an accession number of KCCM11016P, Korean Patent Registration Number 10-0159812), the prepared vector was transformed and smeared to a composite plate medium below.

<Composite Plate Medium>

Glucose 20 g, (NH$_4$)$_2$SO$_4$ 50 g, peptone 10 g, yeast extract 5 g, urea 1.5 g, KH$_2$PO$_4$ 5 g, K$_2$HPO$_4$ 10 g, MgSO$_4$ 7H$_2$O 0.5 g, biotin 100 thiamine chloride salt 1,000 calcium-pantothenic acid 2,000 nicotinamide 2,000 agar 20 g, and kanamycin 25 mg (1 L of distilled water).

About 10,000 colonies were seeded to each of 300 μL of selection media and cultured for about 16 hours at 1,000 rpm at 32° C. in a 96 deep well plate. In order to analyze the production amount of L-lysine produced during culture, the ninhydrin method was used (*J. Biol. Chem.* 1948. 176:367-388). After the culture was completed, 10 μL of culture supernatant and 190 μL of ninhydrin reaction solution (63% glycerol, 27% ninhydrin solution) were reacted at 65° C. for 30 minutes, absorbance was measured by a spectrophotometer at a wavelength of 570 nm, and compared to absorbance of control group (KCCM11016P/pECCG122), 248 species of variant strain exhibiting similar or increased absorbance were selected. During culture under the condition, since the control group strain had residual sugar of 1 g/L to 2 g/L, sugar consumption rate per control group was fast, and strains with increased lysine producing ability could be selected.

<Selection Medium (pH 8.0)>

Glucose 10 g, ammonium sulfate 5.5 g, MgSO$_4$.7H$_2$O 1.2 g, KH$_2$PO$_4$ 0.8 g, K$_2$HPO$_4$ 16.4 g, biotin 100 thiamine HCl 1,000 calcium-pantothenic acid 2,000 and nicotinamide 2,000 μg (1 L of distilled water standard).

In addition, based on strains of 248 selected species, the method was repeatedly performed. As a result, variant strains of the above 29 species which have an enhanced producing ability of L-lysine by more than 10% compared to KCCM11016P/pECCG122 strain were selected.

Example 3: L-Lysine Producing Ability of Selected Artificial Variant Strains and Analysis of Sugar Consumption Rate L-Lysine producing ability of the strains of the 29 selected species of Example 2 and sugar consumption rate were cultured according to the method below and analyzed.

Each strain was seeded into a 250 mL corner-baffle flask and shake-cultured at 30° C. for 20 hours at 200 rpm. Afterwards, 1 mL of a species culture solution was seeded into a 250 mL corner-baffle flask containing 24 mL of a production medium. Using HPLC, the concentration of L-lysine was analyzed, and in order to measure sugar consumption rate of the strains and productivity thereof, the concentration of remaining sugar concentration among the culture solution per time was measured.

<Species Medium (pH 7.0)>

Glucose 20 g, peptone 10 g, yeast extract 5 g, urea 1.5 g, KH$_2$PO$_4$ 4 g, K$_2$HPO$_4$ 8 g, MgSO$_4$.7H$_2$O 0.5 g, biotin 100 μg, thiamine HCl 1,000 μg, calcium-pantothenic acid 2,000 nicotinamide 2,000 μg (1 L of distilled water standard).

<Production Medium (pH 7.0)>

Glucose 100 g, (NH$_4$)$_2$SO$_4$ 40 g, soybean protein 2.5 g, corn steep solids 5 g, urea 3 g, KH$_2$PO$_4$ 1 g, MgSO$_4$.7H$_2$O 0.5 g, biotin 100 thiamine chloride salt 1,000 calcium pantothenic acid 2,000 nicotinamide 3,000 and CaCO$_3$ 30 g (1 L of distilled water standard).

Among variant strains of 29 species, the concentration of L-lysine compared to the control group was above an equivalent level, and three types of the strains with increased sugar consumption rate and productivity were selected for repeatedly performing the culture and analysis, and the analyzed results are shown in Table 1.

TABLE 1

| Strain number | | Residue sugar (g/L) | | L-Lysine | |
|---|---|---|---|---|---|
| | | 18 hours | 28 hours | (g/L) | Average |
| KCCM11016P/ pECCG122 | 1 | 50.9 | 38.2 | 43.1 | 43.4 |
| | 2 | 51.9 | 39.8 | 42.5 | |
| | 3 | 51.2 | 37.6 | 44.5 | |
| KCCM11016P/3 | 1 | 47.9 | 34.2 | 43.3 | 43.4 |
| | 2 | 48.6 | 33.8 | 43.8 | |
| | 3 | 46.9 | 31.9 | 43.0 | |
| KCCM11016P/94 | 1 | 47 | 33.7 | 44.5 | 44.3 |
| | 2 | 46.7 | 33.6 | 44.3 | |
| | 3 | 44.8 | 32.8 | 44.1 | |
| KCCM11016P/1160 | 1 | 42.2 | 26.8 | 44.2 | 43.9 |
| | 2 | 43.5 | 25.4 | 44.1 | |
| | 3 | 42.9 | 24.3 | 43.5 | |

It was confirmed that the three strains produced L-lysine above the equivalent level of the control group, and the rate of consumption per unit hour was enhanced by improving the fermentation productivity. Among the selected variation strains, strain KCCM11016P/1160 with the most meaningfully enhanced productivity was ultimately selected, and plasmids were extracted to search for nucleotide sequence mutations at the fundamental genetic level that caused sugar consumption rate and productivity increase. Afterwards, nucleotide sequences were analyzed using SEQ ID NOs: 5 and 6. Plasmids derived from KCCM11016P/1160 contained from about 450 bp region upstream of NCgl2440 gene ORF initiation codon to the vicinity of about 350 bp downstream of the termination codon. Further, through nucleotide sequence analysis of the gene based on the National Institutes of Health (NIH) GenBank, the gene was confirmed to be gntR1, which is one of gluconate repressors, and gntR1 variation which was introduced to KCCM11016P/1160 strain was substituted from C to T at the 304$^{th}$ nucleotide sequence, and it was confirmed that the 102$^{nd}$ amino acid was mutated from arginine to cysteine.

That is, it was confirmed that arginine, which is the 102$^{nd}$ amino acid of gntR1, having an amino acid sequence of SEQ ID NO: 4, was substituted with cysteine.

Example 4: Vector Preparation for Introducing gntR1 Variation into the Chromosome of L-Lysine Producing Strain In order to confirm the application effect of gntR1 variation which was confirmed in Example 3, a vector which can introduce the same into chromosome was prepared.

Based on reported nucleotide sequences, a primer (SEQ ID NO: 7), in which EcoRI restriction enzyme region was inserted to the 5' end and SalI restriction enzyme region was inserted to the 3' end, was synthesized. Using such primer pairs, PCR was performed by having a plasmid of KCCM11016P/1160 as a mold to amplify gntR1 gene fragments. The PCR condition was repeating 30 times a cycle of denaturing at 94° C. for 5 minutes, denaturing at 94° C. for 30 seconds, annealing at 56° C. for 30 seconds, and polymerizing at 72° C. for 40 seconds, and a polymerization reaction was performed at 72° C. for 7 minutes.

SEQ ID NO: 7:
AAGAATTCAGCAGATCGAAGAAGAAGC

SEQ ID NO: 8:
AAGTCGACGGGACTAAAAGCTGGCG

After treating gene fragments which were amplified with PCR with restriction enzymes EcoRI and SalI, each DNA fragment was obtained, and after connecting the same to pDZ vector (Korean Patent Registration Number 10-0924065) having restriction enzymes EcoRI and SalI ends, it was transformed to *E. coli* DH5a and blotted out on an LB solid medium containing kanamycin (25 mg/L). After selecting a colony which was transformed with a vector in which the target gene was inserted through PCR, a plasmid was obtained using a commonly known plasmid extraction method, and according to the variation which was inserted in gntR1 of the plasmid, it was named pDZ-gntR1 (R102C).

Example 5: Preparation of Strain in which gntR1 Variation is Introduced into KCCM11016P, an L-Lysine Production Strain, and Comparison of Productivity A novel variant introduction vector prepared in Example 4 was transformed into *Corynebacterium glutamicum* KCCM11016P, which is an L-lysine production strain, according to two-step homologous chromosome recombination. Afterwards, the strain in which gntR1 variation on chromosome was introduced was selected according to chromosome sequence analysis, and the strain in which the gntR1 variation was introduced was named as KCCM11016P::gntR1(R102C).

By culturing with same methods as in Example 3, the concentration of L-lysine and residual sugar concentration were measured therefrom. In addition, in order to confirm culture effects from raw sugar, raw sugar production media instead of glucose production media were used to analyze using the same methods [Table 2].

<Original Sugar Production Medium (pH 7.0)>

Raw sugar 100 g, $(NH_4)_2SO_4$ 40 g, soybean protein 2.5 g, corn steep solids 5 g, enzyme 3 g, $KH_2PO_4$ 1 g, $MgSO_4.7H_2O$ 0.5 g, biotin 100 µg, thiamine chloride acid salt 1,000 µg, calcium-pantothenic acid 2,000 µg, nicotinamide 3,000 µg, $CaCO_3$ 30 g (1 L level of distilled water).

TABLE 2

|  | Strain number |  | Residual sugar (g/L) 18 hours | Residual sugar (g/L) 28 hours | L-Lysine (g/L) | Average |
|---|---|---|---|---|---|---|
| Sugar | KCCM11016P | 1 | 47.1 | 32.5 | 43.8 | 43.5 |
|  |  | 2 | 46.2 | 33.8 | 42.6 |  |
|  |  | 3 | 45 | 32.0 | 44.1 |  |
|  | KCCM11016P::GntR1(R102C) | 1 | 34.5 | 21.4 | 43.5 | 43.9 |
|  |  | 2 | 39.5 | 21.2 | 44.2 |  |
|  |  | 3 | 37 | 20.6 | 43.9 |  |
| Raw sugar | KCCM11016P | 1 | 42.9 | 28.6 | 47.3 | 47.0 |
|  |  | 2 | 42.0 | 29.1 | 46. |  |
|  |  | 3 | 41.0 | 28.4 | 47.6 |  |
|  | KCCM11016P::GntR1(R102C) | 1 | 34.1 | 17.2 | 47 | 47.4 |
|  |  | 2 | 35.2 | 16.3 | 47.7 |  |
|  |  | 3 | 33.7 | 15.6 | 47.4 |  |

As a result, it was confirmed that sugar consumption rate was increased without affecting L-lysine production ability KCCM11016P::gntR1(R102C) more than KCCM11016, which is a comparison group in glucose and original sugar media. Further, as a result of confirming time points when all of glucose and original sugar were consumed, comparison groups were completely consumed after 72 hours and 68 hours, and L-lysine was produced at 43.5 g/L and 47.0 g/L, respectively, and gntR1 variation introduction strains were produced at 43.9 g/L and 47.4 g/L after 60 hours and 58 hours. That is, in a case of strains in which gntR1 variation is introduced, it was confirmed that production ability of L-lysine according to time was increased by 21% and 18% with glucose and raw sugar, respectively [Table 3].

TABLE 3

|  | Strain number | Production ability (g/h) | % |
|---|---|---|---|
| Glucose | KCCM11016P | 0.60 | 100 |
|  | KCCM11016P::gntR1(R102C) | 0.73 | 121 |
| Raw sugar | KCCM11016P | 0.69 | 100 |
|  | KCCM11016P::gntR1(R102C) | 0.82 | 118 |

As can be seen from the above results, the introduction of gntR1 variation has L-lysine producing ability at the same level and is effective in glucose and raw sugar consumption rates. That is, when gntR1 variation was introduced of the present invention, it suggests excellence of effectiveness in L-lysine production ability. As such, the present inventors named KCCM11016P::gntR1(R102C) as *Corynebacterium glutamicum* "CA01-2293", which has enhanced glucose consumption rate and productivity, and as of Dec. 5, 2014, it was given an accession number of KCCM11628P, which is deposited at the Korea Culture Center of Microorganisms (KCCM), an international depository institution.

Example 6: Preparation of Strains in which gntR1 Variation is Introduced in L-Lysine Production Strain and Comparison of Productivity In order to determine effects of other strains belonging to *Corynebacterium glutamicum*, a strain in which gntR1 variation is introduced into *Corynebacterium glutamicum* KCCM11347P (the microorganism is disclosed as KFCC10750 and redeposited in an international depository institution under the Budapest Treaty and assigned KCCM11347P. Korean Patent Registration Number 10-0073610) was prepared and named KCCM11347P::gntR1(R102C). Using the same method as in Example 5, the prepared strains were cultured, and lysine production ability and residual sugar were compared [Table 4].

TABLE 4

|  | Strain number |  | Residual sugar (g/L) | | L-Lysine | |
|---|---|---|---|---|---|---|
|  |  |  | 18 hours | 28 hours | (g/L) | Average |
| Glucose | KCCM11347P | 1 | 43.8 | 27.6 | 38.5 | 38.6 |
|  |  | 2 | 42.6 | 28.8 | 38.7 |  |
|  |  | 3 | 43.2 | 27.2 | 38.6 |  |
|  | KCCM11347P::gntR1(R102C) | 1 | 39.2 | 18.2 | 38.6 | 38.7 |
|  |  | 2 | 37.6 | 18.0 | 38.6 |  |
|  |  | 3 | 37.0 | 17.5 | 38.9 |  |
| Residue sugar | KCCM11347P | 1 | 39.9 | 24.9 | 41.2 | 41.3 |
|  |  | 2 | 39.3 | 25.3 | 41.4 |  |
|  |  | 3 | 38.8 | 24.7 | 41.3 |  |
|  | KCCM11347P::gntR1(R102C) | 1 | 35.7 | 14.4 | 41.3 | 41.4 |
|  |  | 2 | 34.2 | 13.7 | 41.3 |  |
|  |  | 3 | 33.3 | 13.1 | 41.6 |  |

As a result, same as in Example 5, it was confirmed that all glucose consumption rates were increased in glucose and raw sugar compared to the comparison group. Further, as a result of determining time points at which glucose and raw sugar were all consumed, the comparison group all consumed sugar at 72 hours and 69 hours, and L-lysine was produced at 38.6 g/L and 41.3 g/L, and gntR1 variation produced L-lysine at 61 hours and 58 hours at 38.7 g/L and 41.4 g/L. That is, in a case of strains wherein gntR1 variation is introduced, the productivity of L-lysine according to time was confirmed to be increased by 18% and 19% in glucose and raw sugar, respectively [Table 5].

TABLE 5

|  | Strain number | Productivity (g/h) | % |
|---|---|---|---|
| Glucose | KCCM11347P | 0.54 | 100 |
|  | KCCM11347P::gntR1(R102C) | 0.63 | 118 |
| Raw sugar | KCCM11347P | 0.60 | 100 |
|  | KCCM11347P::gntR1(R102C) | 0.71 | 119 |

Example 7: Preparation of Strain in which gntR1 Variation is Introduced in L-Lysine Production Strain CJ3P and Comparison of Productivity In order to confirm effects in other strains belonging to *Corynebacterium glutamicum*, a strain in which gntR1 variation is introduced in *Corynebacterium glutamicum* CJ3P (Binder et al. *Genome Biology* 2012, 13: R40) was prepared, and it was named as CJ3P::GntR1(R102C). CJ3P strain is a *Corynebacterium glutamicum* strain having L-lysine producing ability in which 3 types of variations (pyc (Pro458Ser), hom(Val59Ala), lysC(Thr311Ile)) were introduced in wild-type strains based on a disclosed technique. A strain which is prepared using the same method as in Example 5 was prepared, and the producing ability of lysine and concentration of residual sugar in a culture solution per time was measured [Table 6].

TABLE 6

|  | Strain number |  | Residual sugar (g/L) | | L-Lysine | |
|---|---|---|---|---|---|---|
|  |  |  | 12 hours | 18 hours | (g/L) | Average |
| Glucose | CJ3P | 1 | 37.2 | 23.6 | 8.1 | 8.2 |
|  |  | 2 | 37.9 | 23.0 | 8.2 |  |
|  |  | 3 | 37.4 | 21.1 | 8.2 |  |
|  | CJ3P::gntR1(R102C) | 1 | 35.0 | 17.7 | 8.4 | 8.4 |
|  |  | 2 | 35.5 | 17.5 | 8.3 |  |
|  |  | 3 | 34.2 | 16.7 | 8.4 |  |
| Raw sugar | CJ3P | 1 | 34.3 | 21.5 | 8.7 | 8.8 |
|  |  | 2 | 34.1 | 20.9 | 8.8 |  |
|  |  | 3 | 32.7 | 19.2 | 8.8 |  |
|  | CJ3P::gntR1(R102C) | 1 | 30.8 | 16.1 | 9.0 | 9.0 |
|  |  | 2 | 31.8 | 15.9 | 8.9 |  |
|  |  | 3 | 31.3 | 15.2 | 9.0 |  |

As a result, similar to Examples 5 and 6, it was confirmed that sugar consumption rate was increased in gntR1 variation insertion strain compared to the control group. Further, as a result of confirming the time point at which glucose and raw sugar were all consumed, glucose and raw sugar were completely consumed at 48 hours and 42 hours in the control group, and L-lysine was produced at 8.2 g/L and 8.8 g/L, respectively, and gntR1(R102C) insertion strain produced lysine at 42 hours and 38 hours at 8.4 g/L and 9.0 g/L, respectively. That is, in a case of a strain, gntR1 variation is introduced, it was confirmed that the production rate of L-lysine according to time increased by 17% and 13%, respectively [Table 7].

TABLE 7

|  | Strain | Production rate (g/h) | % |
|---|---|---|---|
| Glucose | CJ3P | 0.17 | 100 |
|  | CJ3P::gntR1(R102C) | 0.20 | 117 |
| Raw sugar | CJ3P | 0.21 | 100 |
|  | CJ3P::gntR1(R102C) | 0.24 | 113 |

Accordingly, from the above results, when gntR1 variation was introduced in lysine production strain in the *Corynebacterium* genus, it was confirmed that due to an increase in sugar consumption rate, lysine production rate was effectively enhanced.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. An isolated and/or recombinant polypeptide having gluconate repressor activity comprising the amino acid sequence of SEQ ID NO: 1.

2. An isolated and/or recombinant polynucleotide encoding the polypeptide of claim 1.

3. The isolated and/or recombinant polynucleotide of claim 2, wherein the polynucleotide comprises the nucleotide sequence of SEQ ID NO: 2.

4. An expression vector comprising the polynucleotide of claim 2.

5. A microorganism of the genus *Corynebacterium* producing L-lysine, expressing the polypeptide of claim 1.

6. The microorganism of the genus *Corynebacterium* of claim 5, wherein the microorganism of the genus *Corynebacterium* is *Corynebacterium glutamicum*.

7. A method for producing L-lysine, comprising
 (a) culturing the microorganism of the genus *Corynebacterium* of claim 5 in a medium; and
 (b) recovering L-lysine from the cultured microorganism or the medium in step (a).

8. A method for producing L-lysine, comprising
 (a) culturing the microorganism of the genus *Corynebacterium* of claim 6 in a medium; and
 (b) recovering L-lysine from the cultured microorganism or the medium in step (a).

* * * * *